United States Patent
Clark

(10) Patent No.: US 11,660,234 B2
(45) Date of Patent: *May 30, 2023

(54) SOUND ATTENUATION DEVICES

(71) Applicant: John Clark, Washington, DC (US)

(72) Inventor: John Clark, Washington, DC (US)

( * ) Notice: Subject to any disclaimer, the term of this patent is extended or adjusted under 35 U.S.C. 154(b) by 136 days.

This patent is subject to a terminal disclaimer.

(21) Appl. No.: 17/236,293

(22) Filed: Apr. 21, 2021

(65) Prior Publication Data

US 2021/0236340 A1 Aug. 5, 2021

Related U.S. Application Data

(63) Continuation of application No. 16/537,647, filed on Aug. 12, 2019, now Pat. No. 11,013,637.

(51) Int. Cl.
*A61F 11/00* (2022.01)
*A61F 11/10* (2006.01)
*A61F 11/08* (2006.01)

(52) U.S. Cl.
CPC ............. *A61F 11/10* (2013.01); *A61F 11/085* (2022.01)

(58) Field of Classification Search
CPC ........ A61F 11/10; A61F 11/085; A61F 11/06; A61F 11/12; H04R 1/10; H04R 1/1083
See application file for complete search history.

(56) References Cited

U.S. PATENT DOCUMENTS

| | | | | |
|---|---|---|---|---|
| 4,540,063 A * | 9/1985 | Ochi | ........................ | A61F 11/08 181/135 |
| 4,564,009 A * | 1/1986 | Brinkhoff | ............... | A61F 11/08 128/864 |
| 7,107,993 B2 * | 9/2006 | Magidson | ............... | A61F 11/08 181/129 |
| 7,984,716 B2 * | 7/2011 | Purcell | .................... | A61F 11/08 128/865 |
| 2006/0050912 A1 * | 3/2006 | Kidd | .................... | H04R 25/656 381/328 |
| 2007/0183606 A1 * | 8/2007 | Doty | ........................ | A61F 11/12 381/72 |
| 2013/0126262 A1 * | 5/2013 | Wilmink | ................. | A61F 11/08 181/135 |
| 2020/0276054 A1 * | 9/2020 | Leight | ..................... | A61F 11/08 |

* cited by examiner

*Primary Examiner* — Steven O Douglas

(57) ABSTRACT

Sound attenuation devices are provided that may be temporarily worn in a person's ear. The devices generally include a first flange that is configured to be disposed in a person's ear; a second flange that is positioned proximate to the first flange and is also configured to be disposed in the person's ear (with the second flange having a proximate end that exhibits an oblong perimeter); and a cylindrical shaft extending from an interior portion of the second flange. The shaft includes an integrally connected pull tab; it extends beyond the proximate end of the second flange; and the shaft includes an integrally formed reinforcing member that spans an exterior side of the shaft and at least a portion of the pull tab. The devices further include a sound filter disposed within an internal cavity of the shaft.

7 Claims, 5 Drawing Sheets

Bunching

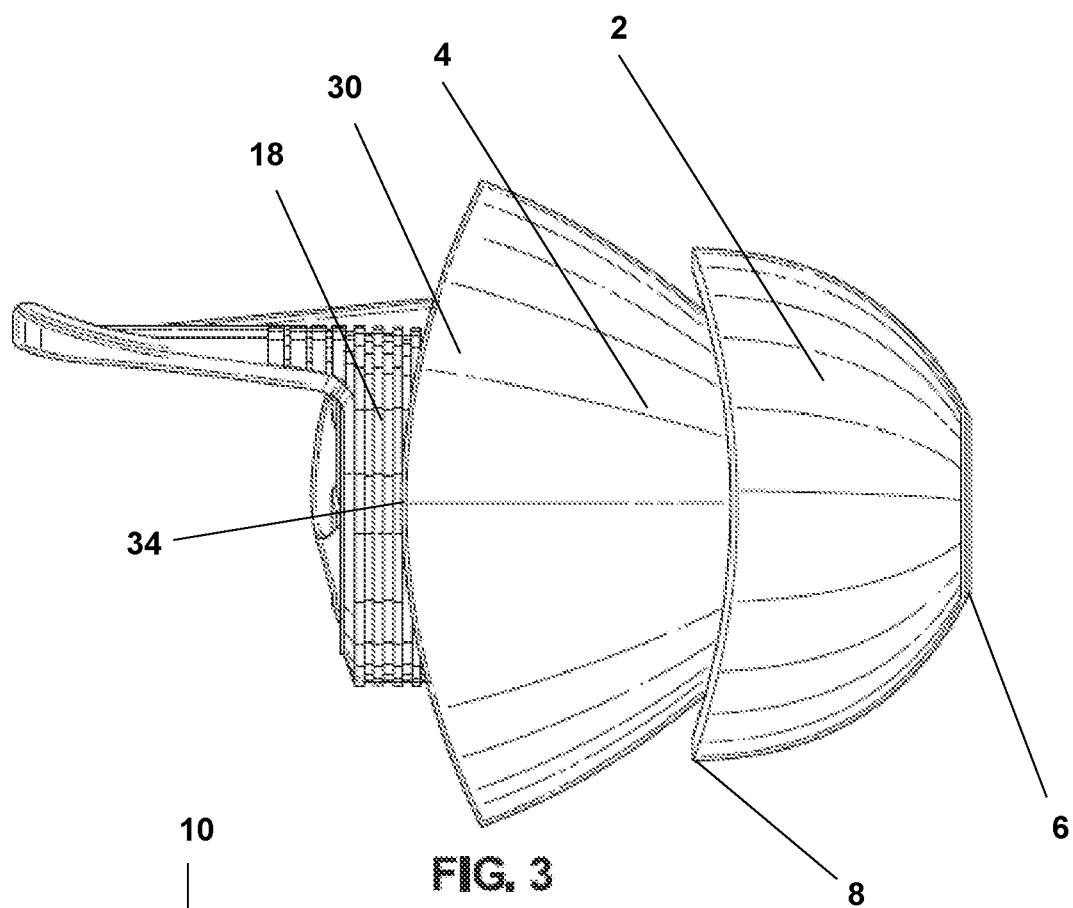
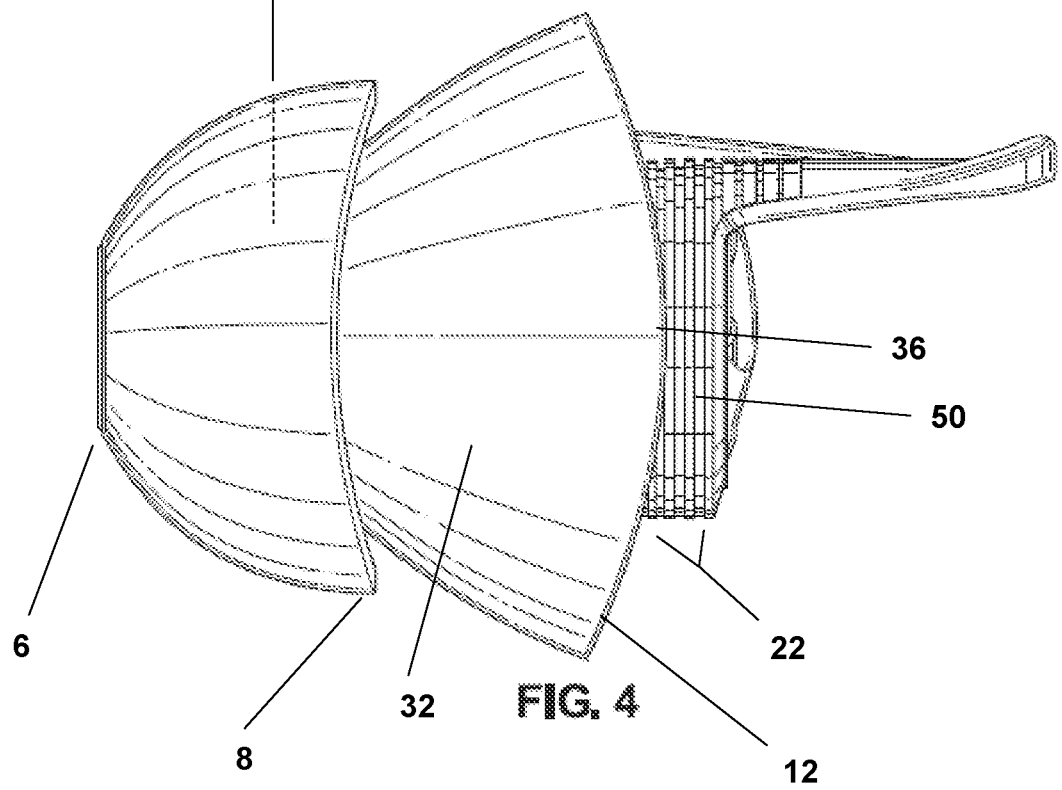

Length (y) of Back Side 38

SOUND ATTENUATION DEVICES

CROSS-REFERENCE TO RELATED APPLICATIONS

This application is a continuation of U.S. patent application Ser. No. 16/537,647, filed on Aug. 12, 2019.

FIELD OF THE INVENTION

The field of the present invention relates to devices and methods for attenuating sounds. More particularly, the field of the present invention relates to devices that are disposed in a person's ear for the purpose of attenuating loud sounds and avoiding temporary and/or permanent hearing damage. In addition, the field of the invention relates to methods for avoiding temporary and/or permanent hearing damage, which involve the use of the devices described herein.

BACKGROUND OF THE INVENTION

For years, individuals have used ear plugs to minimize the distraction of unwanted sounds, such as when students take exams in school, or when individuals wish to sleep on airplanes. In addition, ear plugs are often used to avoid temporary and/or permanent hearing damage that may result from being exposed to extremely loud sounds or noises, such as during live music concerts, motorsport events, or when using loud industrial machinery. Indeed, ear plugs have been used for many years in these, and other, types of situations.

A common type of ear plug used today comprises a soft, cylindrical-shaped material, which may be compressed and inserted into a person's ear. While such conventional ear plugs provide some level of sound attenuation, they suffer from many drawbacks. For example, many of such prior art ear plugs do not permit a desirable amount of sound into a person's inner ear, e.g., in the case of a person who is attending a music concert (who wants to mitigate the risk of hearing loss, but still hear the music as close to its original sound signature as possible, or otherwise wants a flat attenuation response). Furthermore, in many cases, the ear plugs will not remain lodged in a person's ear, and may inadvertently fall out. In addition, these ear plugs are often difficult to insert into, and then remove at a desirable time, from a person's inner year.

Other types of prior art ear plugs may employ the use of circular and flexible flanges (instead of the more basic soft, cylindrical-shaped prior art ear plugs mentioned above). Unfortunately, even those prior art ear plugs also suffer from various drawbacks. For example, such prior art ear plugs typically have circular flanges—and it is often assumed that such flanges will deform upon insertion into a person's ear canal (to properly seal the ear canal). However, that is not the case. The circular flanges of such prior art ear plugs often "bunch" in a person's ear canal, which compromises the ability of the ear plug to properly seal within the ear due to the presence of slit leaks (and, moreover, creates some discomfort for the person wearing the ear plug). That is, this mismatch between the shape of the flanges/ear plug and the internal area of an ear canal causes the material of the flanges to "bunch" and/or fold, which results in micro-leak passages of sound via diffraction. These prior art ear plugs may also employ the use of 3-4 flanges, which intrude deeper into an ear canal than is necessary to create a proper seal (which often causes irritation to delicate ear canal tissues).

The present invention addresses the foregoing problems, and others, which are associated with the sound attenuation devices that are currently available in the marketplace.

SUMMARY OF THE INVENTION

According to certain aspects of the present invention, sound attenuation devices are provided that may be temporarily worn in a person's ear, for the purpose of avoiding or minimizing temporary and/or permanent hearing loss (or otherwise reducing the audibility of particular sounds). The devices generally comprise a first flange that is configured to be disposed in a person's ear and a second flange that is positioned proximate to the first flange and is also configured to be disposed in the person's ear. The invention provides that both of the first and second flanges have a proximate end and a distal end, with the proximate ends having an oblong (non-circular) perimeter. The devices further include a cylindrical shaft that extends from an interior portion of the second flange. The shaft includes an integrally connected pull tab; it extends beyond the proximate end of the second flange; and it preferably includes an integrally formed reinforcing member that spans an exterior side of the shaft and at least a portion of the pull tab. The devices of the present invention further include a sound filter disposed within an internal cavity of the shaft.

According to other aspects of the invention, methods for attenuating particular sounds and noise are provided, along with methods of avoiding temporary and/or permanent hearing loss. The methods of the present invention generally comprise disposing a device of the present invention, as described herein, in each ear of a person, prior to (or shortly following) being subjected to loud sounds.

The above-mentioned and additional features of the present invention are further illustrated in the Detailed Description contained herein.

BRIEF DESCRIPTION OF THE FIGURES

FIG. 3 is a right side view of the sound attenuation devices described herein.

FIG. 4 is a left side view of the sound attenuation devices described herein.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

Figure 1:
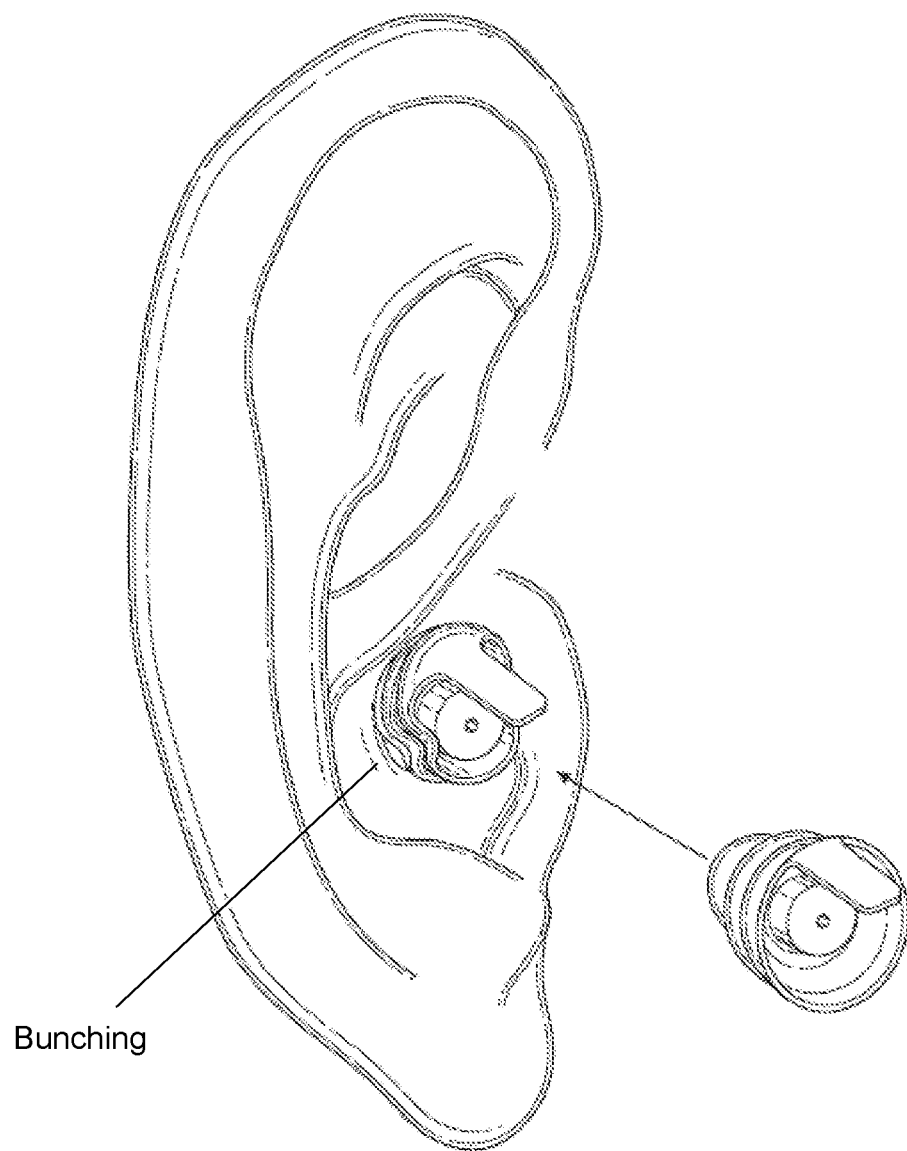
FIG. 1 is an illustration of a prior art ear plug being disposed in a person's ear, which further shows the unwanted "bunching" that occurs with certain prior art ear plugs.
Figure 2:
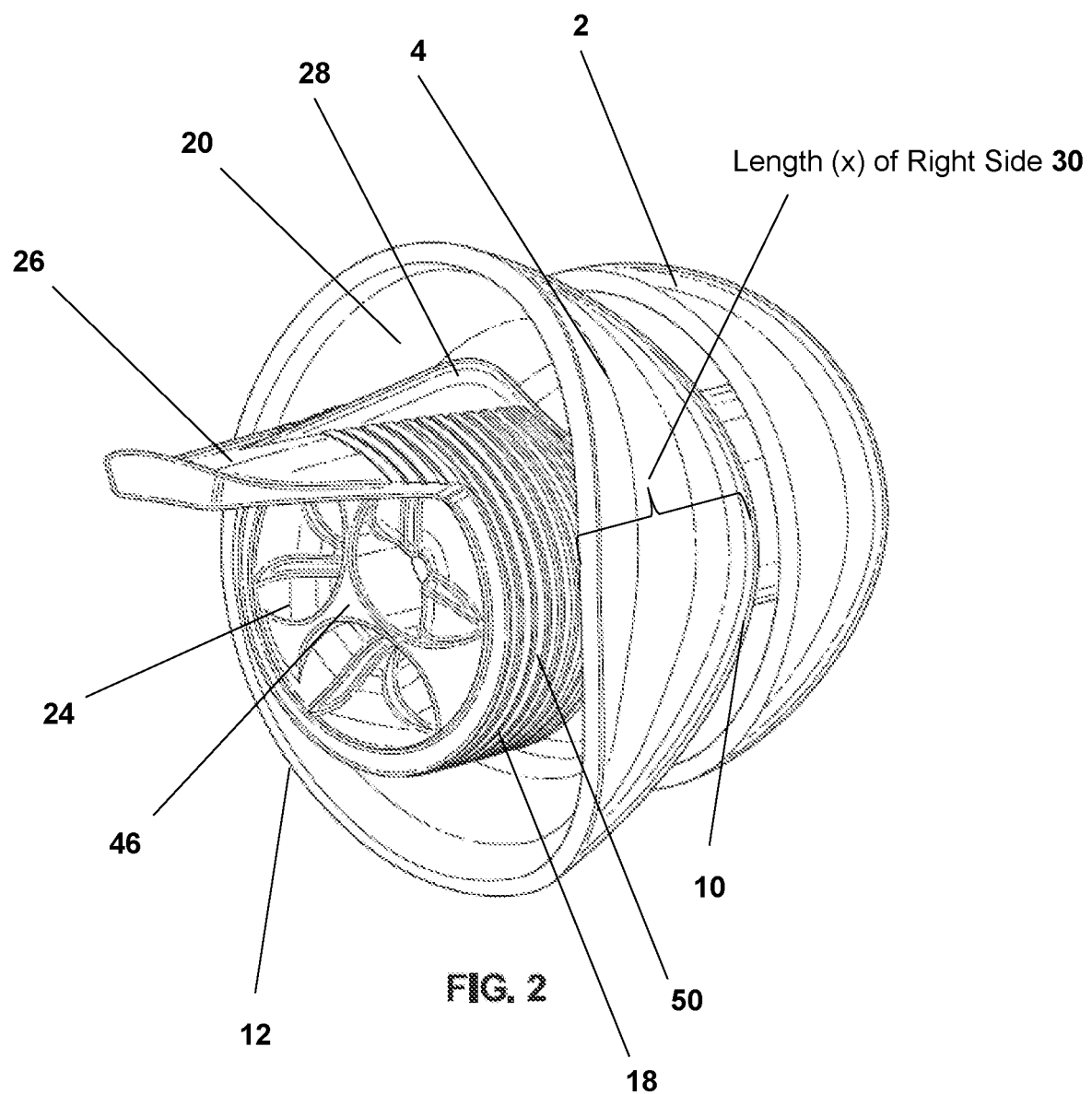
FIG. 2 is a perspective view of the sound attenuation devices described herein.

According to certain preferred embodiments of the present invention, sound attenuation devices are provided that may be temporarily worn in a person's ear. Such devices may be worn for the purpose of avoiding or minimizing temporary and/or permanent hearing loss, or otherwise reducing the level of audible sounds. In addition, the sound attenuation devices of the present invention seek to minimize or avoid unwanted "bunching" when the device is inserted into a person's ear canal. To explain this feature, FIG. 1 provides an illustration of a prior art ear plug, which—when disposed in an ear canal—produces unwanted "bunching," i.e., the side of the ear plug does not adequately conform to the internal dimensions of a typical ear canal, which causes the sides of the ear plug to fold and bunch. This unwanted "bunching" results in gaps forming between the exterior side of the ear plug and the ear canal, such that sound is allowed to enter the ear canal (unfiltered) through such gaps. This compromises the ability of the ear plug to properly filter sound and, furthermore, creates discomfort for the person wearing the ear plug. The sound attenuation devices of the present invention avoid this problem that is otherwise inherent with prior art ear plugs (and, furthermore, the sound attenuation devices provide many other benefits not provided by such prior art ear plugs).

Figure 5:
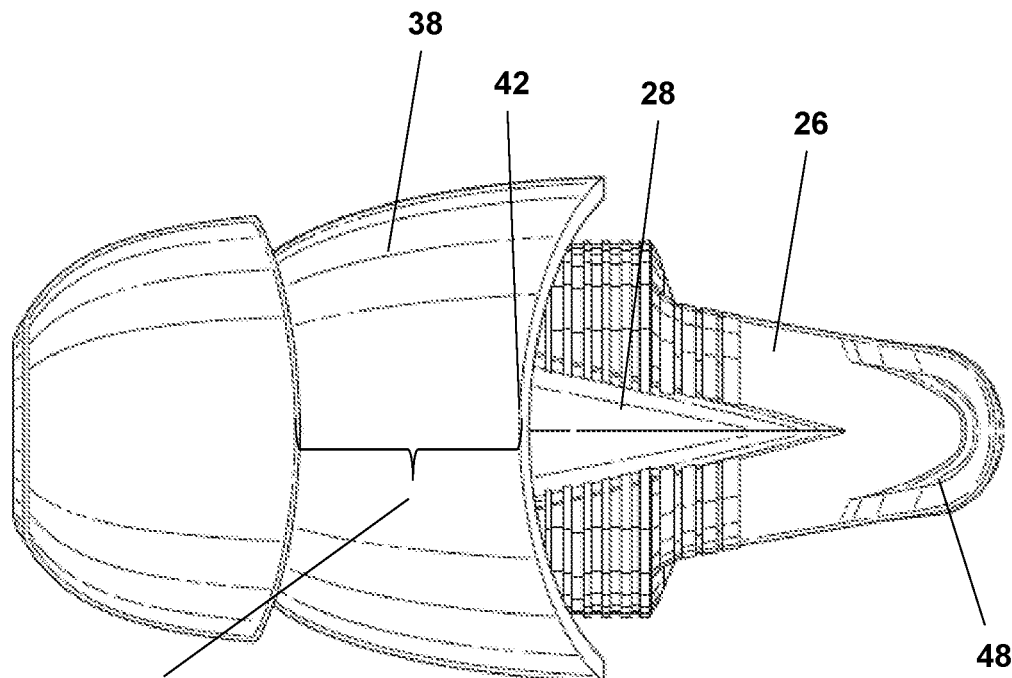
FIG. 5 is a back side view of the sound attenuation devices described herein.
Figure 6:
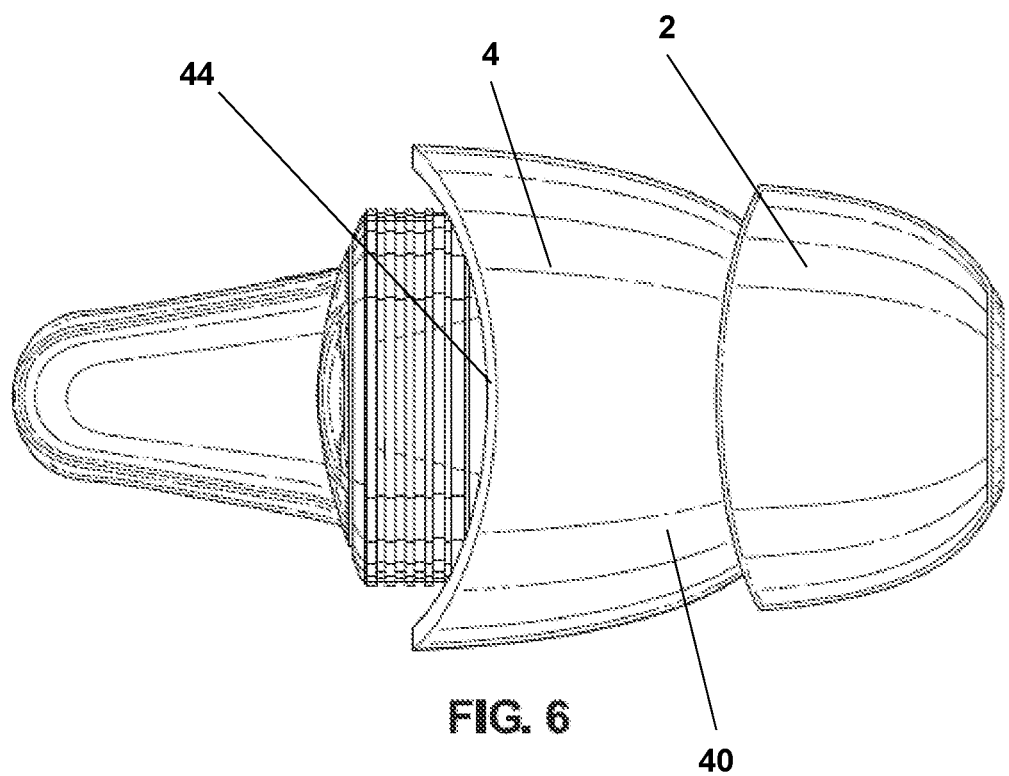
FIG. 6 is a front side view of the sound attenuation devices described herein.
Figure 7:
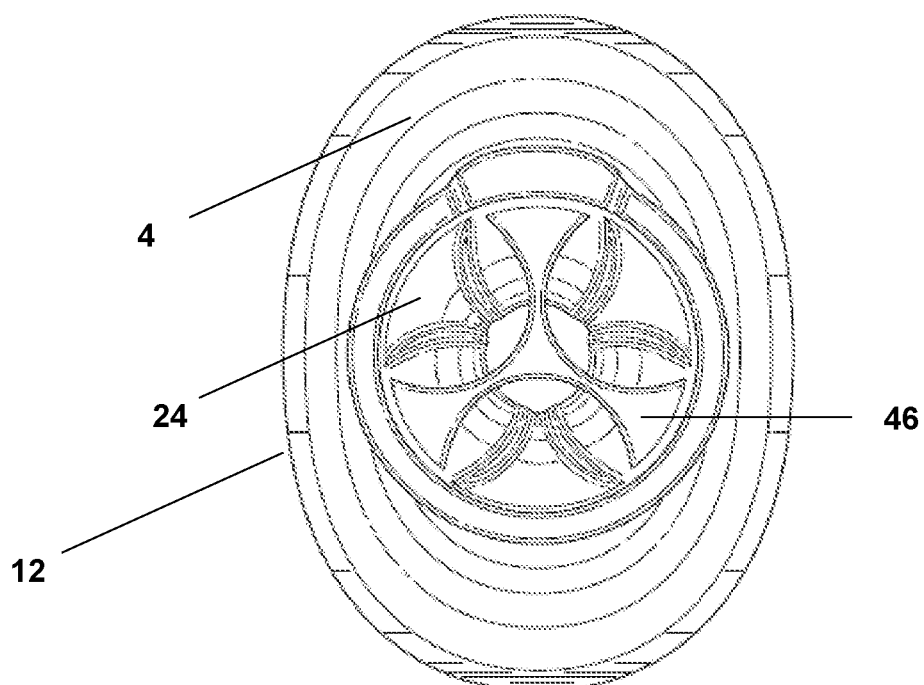
FIG. 7 is a bottom view of the sound attenuation devices described herein.
Figure 8:
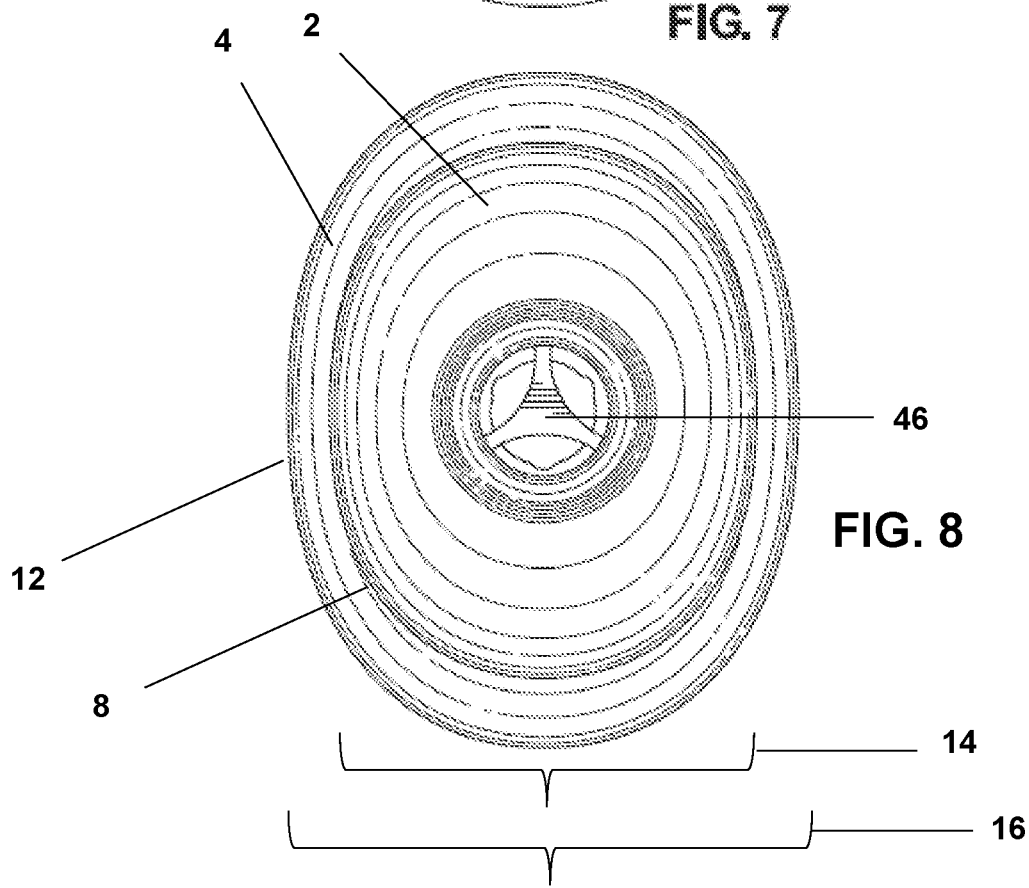
FIG. 8 is a top view of the sound attenuation devices described herein.

Referring now to FIGS. 2-8, the sound attenuation devices of the present invention generally comprise a first flange 2 and a second flange 4 that are configured to be disposed in a person's ear. The invention provides that the first flange 2 and the second flange 4 exhibit a dome-like configuration, with the top (apex) portion thereof, also referred to herein as the distal end 6, leading as the device is inserted into a person's ear. More particularly, the invention provides that the first flange 2 includes its own distal end 6 and its own proximate end 8. Likewise, the invention provides that the second flange 4 includes its own distal end 10 (which partially resides within the interior area of the first flange 2) and its own proximate end 12. Referring now to FIGS. 7 and 8, the invention provides that the proximate end 12 of the second flange 4 exhibits an oblong perimeter—i.e., an oval (non-circular) shape. Similarly, according to certain preferred embodiments, the proximate end 8 of the first flange 2 also exhibits an oblong perimeter—i.e., an oval (non-circular) shape. The invention provides that such configuration facilitates the sound attenuation device being inserted into a person's ear canal, without the sides of the first flange 2 and second flange 4 "bunching" as described above (and illustrated in FIG. 1, with respect to a prior art ear plug).

Still further, in certain embodiments, the invention provides that the second flange 4 (and first flange 2) exhibits yet additional structural features that help prevent "bunching" in an ear canal. More particularly, for example, the second flange 4 includes four general sides, with a first pair of sides (the left and right sides) being longer than the other two sides (the front and back sides). This difference can be viewed by comparing FIGS. 3 and 4 to FIGS. 5 and 6. More particularly, in certain preferred embodiments, the lengths (x) (FIG. 2) of the right side 30 (FIG. 3) and left side 32 (FIG. 4) of the second flange 4 are identical, when measured at a center location 34/36 of each side. Likewise, as illustrated in FIGS. 5 and 6, the lengths (y) of the back side 38 (FIG. 5) and front side 40 (FIG. 6) of the second flange 4 are identical, when measured at a center location 42/44 of each side. The invention provides, in such embodiments, the lengths (y) of the back side 38 (FIG. 5) and front side 40 (FIG. 6) are shorter than the lengths (x) of the right side 30 (FIG. 3) and left side 32 (FIG. 4). The invention provides that such configuration, when applied to the second flange 4 (as well as the first flange 2), also contributes to avoiding unwanted "bunching" when the device is inserted into a person's ear canal.

More particularly, the configuration described in the preceding paragraph, as it relates to the four general sides of the first flange 2 and second flange 4, produces certain contours that form a wave around the edges (or proximate perimeters) of the flanges 2/4—or, described another way, it produces a crest and a trough along the edges (or proximate perimeters) of the flanges 2/4. Although the foregoing describes the configuration of the second flange 4 (with reference to the Figures), the invention provides that the first flange 2 will also, preferably, exhibit the same configuration, i.e., consist of four general sides, with a first pair of sides (the left and right sides) being longer than the other two sides (the front and back sides), such that a crest and a trough form along the edge (or proximate perimeter) of the flange 2.

The invention provides that, upon insertion into a person's ear canal, such configuration enables the first flange 2 and second flange 4 to expand and immediately conform to the inner dimensions of the ear canal—which, as described above, creates an enhanced fit and avoids unwanted "bunching." More particularly, in the configuration described herein, the first flange 2 rests inside a narrower oval-shaped portion of the ear canal, compared to the position of the second flange 4. The invention provides that, when such configuration is employed, the high point of the contour (of the first flange 2) first contacts the top of the ear canal, which forces the first flange 2 to expand. Because of the contoured design, the low point of such contour contacts the ear canal with less material (compared to prior art ear plugs), thereby minimizing unwanted bunching and slit leaks. The invention provides that the second flange 4 makes contact with a larger portion of the ear canal, such that additional material is required to effectively seal that area of the canal. The invention provides that the low part of the second flange 4 is configured to enter the ear canal first, which forces the high part of the second flange 4 to expand, to thereby effectively seal the second flange 4 within the ear canal.

Still further, according to certain preferred embodiments, the invention provides that the first flange 2 will preferably exhibit a smaller size than that of the second flange 4. For example, in certain embodiments of the invention, the first flange 2 may exhibit a width 14 of about 9-12 mm, whereas the second flange 4 may exhibit a width 16 of about 12-15 mm (FIG. 8). The invention provides that this configuration also assists in avoiding unwanted "bunching" when the device is inserted into a person's ear canal.

According to certain preferred embodiments of the present invention, the devices further comprise a shaft 18 extending from an interior portion 20 of the second flange 4. In certain embodiments of the present invention, the shaft 18 preferably extends beyond the proximate end 12 of the second flange 4 by a particular distance 22 (FIG. 4). More particularly, for example, the shaft 18 may extend beyond the proximate end 12 of the second flange 4 by about 6 mm or, alternatively, by no more than about 4 mm or, in other embodiments, by no more than about 2 mm. According to certain embodiments, the invention provides that the shaft 18 comprises a series of parallel grooves 50 along a circumference/perimeter of the exterior side of the shaft 18. The invention provides that the series of parallel grooves 50 (or, stated another way, series of parallel protruding ribs that form the grooves 50) imparts additional structural integrity to the shaft 18, while also limiting the amount of material (and thus) total weight of the shaft 18.

The invention further provides that the shaft 18 is preferably cylindrical in shape (although other geometric configurations may be employed), and includes an internal cavity 24 in which a plastic sound filter resides. The invention provides that the plastic sound filter (which are generally known and available to those of ordinary skill in the art) will comprise an aperture through which sound waves are permitted to transcend the device and enter a person's inner ear—such aperture may exhibit a diameter that is less than about 1.5 mm or, more preferably, less than about 1.3 mm, such as about 1.0 mm. According to certain preferred embodiments, the internal cavity 24 of the shaft 18 includes a triangular-shaped structural brace 46, which constitutes a part of the sound filter and is connected to or integrally formed with three separate and equally-spaced areas of an interior side of the shaft 18. The invention provides that the presence and position of the triangular-shaped structural brace 46 enhances (1) the structural integrity of the shaft 18 and, importantly, (2) the sound attenuation abilities of the device. More particularly, the invention provides that the presence, location, and configuration of the triangular-shaped structural brace 46 produces a desirably more flattened sound attenuation.

According to further preferred embodiments, the invention provides that the devices will preferably include a pull tab 26, which is integrally formed with the device, such as with the proximate portion of the shaft 18. In certain embodiments, the area at which the pull tab 26 is integrally formed with the proximate portion of the shaft 18 is structurally reinforced, such that the pull tab 26 may be grasped and pulled with a desirable amount of force, e.g., to remove the device from a person's ear canal, without causing the pull tab 26 to break away from the shaft 18 or otherwise compromise the structural integrity of the shaft 18 and device. More particularly, in certain embodiments, the device includes a reinforcing member 28 that protrudes upwards from and spans an exterior side of the shaft 18 (and preferably spans at least a portion of the pull tab 26). In addition, the invention provides that an interior side of the pull tab 26 preferably includes a gripping ridge 48 (FIG. 5), which facilitates a person's gripping and exerting a pull force on the pull tab 26 (e.g., during removal of the device from a person's ear canal).

The invention provides that the device may be comprised of any suitable materials, including, but not limited to, plastics, elastomers, rubbers, other synthetic and natural materials, or combinations of the foregoing. Preferably, however, the device is comprised of a relatively flexible material that can adapt to the contours of a person's inner ear when inserted therein, in order to create a preferably secure and tight fit between the device and the person's ear (without experiencing the unwanted bunching described above). In addition, a device comprised of, for example, a flexible elastomer will be more comfortable to a person than, for example, a substantially rigid material—such as a rigid plastic material. The foregoing makes reference to the filter being comprised of plastic (albeit preferably encased within an elastomer or silicone, such that the plastic material does not make contact with the ear canal). However, those of ordinary skill in the art will appreciate that other compositions and materials may be used to construct the filter, such as elastomers, rubbers, other synthetic and natural materials, or combinations of the foregoing.

According to other aspects of the invention, methods for attenuating unwanted sounds and noises are provided, along with methods of avoiding temporary and/or permanent hearing loss. The methods of the present invention generally comprise inserting a device of the present invention, as described herein, in each ear of a person, prior to being subjected to loud sounds or unwanted sounds. Of course, the device may be inserted into a person's ear prior to the commencement of the sounds, or shortly following the commencement of the sounds. Compared to prior art ear plugs, the devices of the present invention have been found to deliver a specific and more preferred flat-type of sound attenuation experience. Such preferred sound attenuation is achieved by the unique configuration of the device and its ability to avoid "bunching" and slit leaks, as described herein.

The many aspects and benefits of the invention are apparent from the detailed description, and thus, it is intended for the following claims to cover all such aspects and benefits of the invention which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A sound attenuation device, which comprises:
   (a) a first flange that is configured to be disposed in a person's ear;
   (b) a second flange that is positioned proximate to the first flange and is also configured to be disposed in the person's ear, wherein the first flange and second flange each include a proximate end and a distal end, wherein each proximate end exhibits an oblong perimeter;
   (c) a cylindrical shaft extending from an interior portion of the second flange, wherein the shaft (i) includes an integrally connected pull tab and (ii) extends beyond the proximate end of the second flange; and
   (d) a sound filter disposed within an internal cavity of the shaft.

2. The sound attenuation device of claim 1, wherein the shaft further includes an integrally formed reinforcing member that spans an exterior side of the shaft and at least a portion of the pull tab.

3. The sound attenuation device of claim 1, wherein the shaft comprises a series of parallel grooves along a circumference of the exterior side of the shaft.

4. The sound attenuation device of claim 1, wherein the internal cavity of the shaft includes a triangular-shaped structural brace, which forms a part of the sound filter and is connected to or integrally formed with three separate areas of an interior side of the shaft.

5. The sound attenuation device of claim 1, wherein each of the first flange and second flange includes four sides, wherein:
   (a) a first side and a second side have an identical length at a center location of each of the first side and second side;
   (b) a third side and a fourth side have an identical length at a center location of each of the third side and fourth side; and
   (c) the length of the first side and second side is shorter than the length of the third side and fourth side.

6. The sound attenuation device of claim 1, wherein an interior side of the pull tab comprises a gripping ridge.

7. The sound attenuation device of claim 1, wherein the first flange and second flange are each configured to expand and conform to an inner dimension of an ear canal, after being disposed in the person's ear.

\* \* \* \* \*